United States Patent
Catacchio et al.

(10) Patent No.: US 11,090,213 B2
(45) Date of Patent: Aug. 17, 2021

(54) SURGICAL LIMB POSITIONING APPARATUS

(71) Applicant: Smith & Nephew, Inc., Memphis, TN (US)

(72) Inventors: Anthony Catacchio, Littleton, MA (US); Daniel Zahynacz, Somerville, MA (US); William Obendorf, Chelmsford, MA (US); Graham Smith, Newburyport, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 146 days.

(21) Appl. No.: 16/475,844

(22) PCT Filed: Jan. 22, 2018

(86) PCT No.: PCT/US2018/014663
§ 371 (c)(1),
(2) Date: Jul. 3, 2019

(87) PCT Pub. No.: WO2018/140346
PCT Pub. Date: Aug. 2, 2018

(65) Prior Publication Data
US 2019/0350792 A1 Nov. 21, 2019

Related U.S. Application Data (60) Provisional application No. 62/449,724, filed on Jan. 24, 2017.

(51) Int. Cl.
*A61G 13/00* (2006.01)
*A61F 5/37* (2006.01)
*A61G 13/12* (2006.01)

(52) U.S. Cl.
CPC ........ *A61G 13/0072* (2016.11); *A61F 5/3761* (2013.01); *A61G 13/1235* (2013.01); *A61G 2200/54* (2013.01)

(58) Field of Classification Search
CPC ........ A61G 13/08; A61G 13/12; A61G 13/00; A61G 13/124; A61G 13/1235;
(Continued)

(56) References Cited

U.S. PATENT DOCUMENTS 2,720,878 A * 10/1955 Hickman ............. A61G 7/0755
602/28
4,930,523 A * 6/1990 Laico ........................ A61F 5/04
5/87.1

(Continued)

OTHER PUBLICATIONS

European Application No. 18705198.2-1113 Office Action dated Sep. 6, 2019.
(Continued)

*Primary Examiner* — Ophelia A Hawthorne
(74) *Attorney, Agent, or Firm* — Burns & Levinson, LLP; Joseph M. Maraia; Marlo Schepper Grolnic (57) ABSTRACT

An apparatus that controls the rotation of an operative limb during shoulder surgery is composed of three parts: 1) a mechanism that is part of the durable apparatus, and which allows the limb to be suspended from the system and traction weights applied, but is configured in such a manner that the cable or other connecting member does not rotate about its axis; 2) a sterile connector that acts as the interface between the non-sterile durable apparatus and a sterile patient-contacting disposable drape; and 3) the disposable drape which is secured to the patient's operative arm. One of the sterile connector and the disposable drape contains a feature that allows the physician to rotate and hold the limb in any desired position, without requiring that it be manually held in place.

17 Claims, 8 Drawing Sheets

(58) Field of Classification Search
CPC .............. A61G 13/129; A61G 13/1295; A61G 13/126; A61G 13/0036; A61G 13/0045; A61G 13/1255; A61B 46/27; A61B 19/12; A61B 19/00; A61F 5/3761
See application file for complete search history.

(56) References Cited

U.S. PATENT DOCUMENTS 5,003,967 A * 4/1991 McConnell ............ A61G 13/12
2/158
8,540,656 B1 * 9/2013 Powlan ................. A61F 5/3761
602/36

OTHER PUBLICATIONS

Chinese Application No. 201880005963.7—First Office Action dated Feb. 10, 2021.
Chinese Application No. 201880005963.7 Search Report.

* cited by examiner

SURGICAL LIMB POSITIONING APPARATUS

CROSS-REFERENCE TO RELATED APPLICATIONS

This application is the U.S. national phase entry under 35 U.S.C. § 371 of International Application No. PCT/US2018/014663, filed Jan. 22, 2018, entitled SURGICAL LIMB POSITIONING APPARATUS, which in turn claims priority to and benefit of U.S. Provisional Application No. 62/449,724, filed Jan. 24, 2017, the contents of which are incorporated herein by reference in their entirety for all purposes.

FIELD

This disclosure relates generally to devices which are used to position a limb of a patient during a medical procedure, and more particularly to devices which are used to position the shoulder and arm of a patient during shoulder surgery.

BACKGROUND

Orthopedic shoulder surgery involves complexities not encountered in other surgeries, such as knee surgery. For example, during shoulder surgery, ports or incisions are placed through a patient's shoulder joint in order to provide access for instruments such as light sources, visual scopes, and surgical tools. However, it is sometimes desirable for a surgeon to gain access to a different area of the joint, without creating new ports, by rotating the operative limb and holding it in a new position. This is usually done manually by a physician's assistant who must rotate and hold the arm in a new fixed position for as long as needed to allow the surgeon to complete the required tasks. This prevents the assistant from doing anything else during this time, and can result in fatigue for the assistant, leading to inconsistent positioning of the patient's arm.

Specialized mechanical positioning devices have been developed for supporting and positioning body parts during surgery. These devices may include a drape attached to the patient's limb from which a cord is routed through a boom member. The other end of the cord extending from the boom member is selectively weighted to apply tension to the cord and achieve the desired traction on the limb. However, adjusting these devices to obtain a new limb position may still require the use of an assistant, which may preclude optimal positioning of the limb. Furthermore, since maintaining a sterile surgical field during the operation is critical, it is a challenge to bridge the gap between the non-sterile positioning device and the sterile surgical drape.

BRIEF SUMMARY

Described herein is an apparatus that controls the rotation of an operative limb during shoulder surgery which includes a specially-designed, disposable wrap or drape attached to a flexible and non-rotating segment of a limb suspension system. The limb suspension system of this disclosure is composed of three parts: 1) a mechanism that is part of the durable apparatus, and which allows the limb to be suspended from the system and traction weights applied, but is configured in such a manner that the cable or other connecting member does not rotate about its axis; 2) a sterile connector that acts as the interface between the non-sterile, durable apparatus and a sterile, patient-contacting disposable drape; and 3) the disposable drape which is secured to the patient's operative arm. One of the sterile connector and the disposable drape contains a feature that allows the physician to rotate and hold the limb in any desired position, without requiring that it be manually held in place. Advantageously, the apparatus of this disclosure eliminates the need for an assistant while also maintaining a sterile field of operation.

Further examples of the surgical limb positioning apparatus of this disclosure may include one or more of the following, in any suitable combination.

Examples of the surgical limb positioning apparatus of this disclosure include an elongated, hollow boom member having a proximal end, a distal end and a longitudinal axis extending therebetween. The apparatus has a carriage disposed within the boom member and moveable along the longitudinal axis. The apparatus further includes a first flexible member attached to a first side of the carriage and exiting the boom member at a first aperture located at the proximal end of the boom member. A free end of the first flexible member is configured for attachment to a weight. The apparatus further has a second flexible member attached to a second side of the carriage such that the flexible member cannot rotate relative to the longitudinal axis of the boom member. The second flexible member exits the boom member at a second aperture located at the distal end of the boom member. The apparatus yet further includes a connector assembly attached to a free end of the second flexible member for forming a sterile connection to a drape assembly. One of the connector assembly and the drape assembly has an anti-rotation mechanism configured to maintain an operative limb of a patient in a pre-selected position.

In further examples of the apparatus, the boom member is a generally square tube and the carriage is a wheeled carriage. The first flexible member is a wire rope and the second flexible member is a metal cord. The apparatus further includes an arcuate portion attached to the distal end of the boom member. The second flexible member is routed through a plurality of pulleys housed within the arcuate portion. The pulleys provide an additional anti-rotational resistance to the second flexible member. In examples, the connector assembly includes a receiver attached to the free end of the second flexible member and a connector for releasably coupling to the receiver. A first end of the connector includes a pin, and the receiver has an opening for receiving the pin. A second end of the connector comprises a projection, and the drape assembly has an aperture for releasably coupling to the projection. At least a portion of the connector is sterile. In examples, the anti-rotation mechanism is a torque insert disposed within the connector.

Examples of a connector assembly for use with a limb positioning apparatus of this disclosure include a receiver attached to a free end of a flexible member of the limb positioning apparatus and a connector for releasably coupling to the receiver. A first end of the connector includes a pin, and a second end of the connector includes a projection. The receiver has an opening for receiving the pin, while a drape assembly for retaining an operative limb of a patient has an aperture for releasably coupling to the projection. In examples, the projection is a T-shaped projection. The connector has an anti-rotation mechanism configured to maintain the operative limb of the patient in a pre-selected position. In examples, the anti-rotation mechanism is a torque insert disposed within the connector.

Examples of a method of positioning a limb during surgery of this disclosure include disposing an operative limb of a patient within a drape assembly of a limb positioning apparatus as described above and rotating the operative limb of the patient to a pre-selected position. The anti-rotation mechanism is configured to maintain the operative limb of the patient in the pre-selected position. In examples, the anti-rotation mechanism is a torque insert disposed within the connector.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 41A-4B illustrate an example of the sterile connector of the apparatus of FIG. 1;

DETAILED DESCRIPTION

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1:
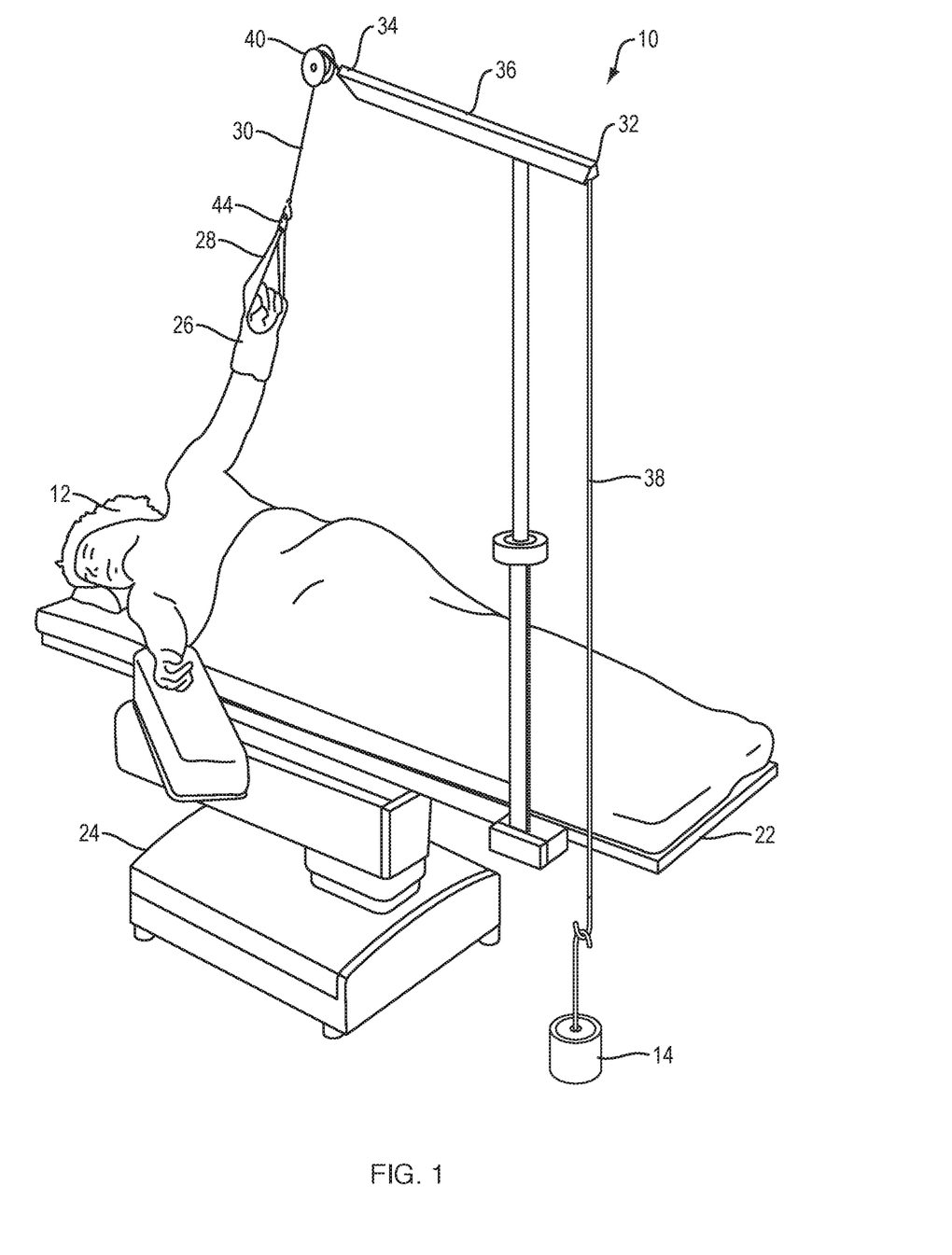
FIG. 1 is a perspective view illustrating the use of the limb positioning apparatus of this disclosure.

Referring now to FIG. 1, an exemplary limb positioning apparatus 10 of this disclosure is illustrated schematically, the component parts of which are described in more detail below. In FIG. 1, a patient 12 is shown lying on a standard operating table 22 and prepared for a surgical operation. The operating table 22 is supported by a suitable stand or support 24 on the floor of the operating room. The forearm of the arm 26 to be operated upon is encased within a sterile surgical drape assembly 28. A non-sterile, flexible drive shaft 30, which may be a metal cord, is secured to the drape assembly 28 and is routed through an elongated boom member 36. The boom member 36 may be in the form of a generally square tube, having a proximal end 32 and a distal end 34. The boom member 36 may be made of stainless steel or other suitable materials for maintaining an easily cleaned exterior surface.

In FIG. 1, the boom member 36 is shown as fixedly secured to the operating table 22. The drive shaft 30 is threaded over a plurality of pulleys 40 at the distal end of the boom member 36 and is attached to the drape assembly 28 via a connector assembly 44. The connector assembly 44 is configured to connect the non-sterile drive shaft 30 and the sterile drape assembly 8, as further described below. Another flexible member, which may be a wire rope 38, extends from the proximal end 32 of the boom member 36 and is configured to attach to selectively applied weights 14 in order to place the drive shaft 30 under tension and achieve the desired traction on the arm 26 of the patient 12.

Figure 2A:
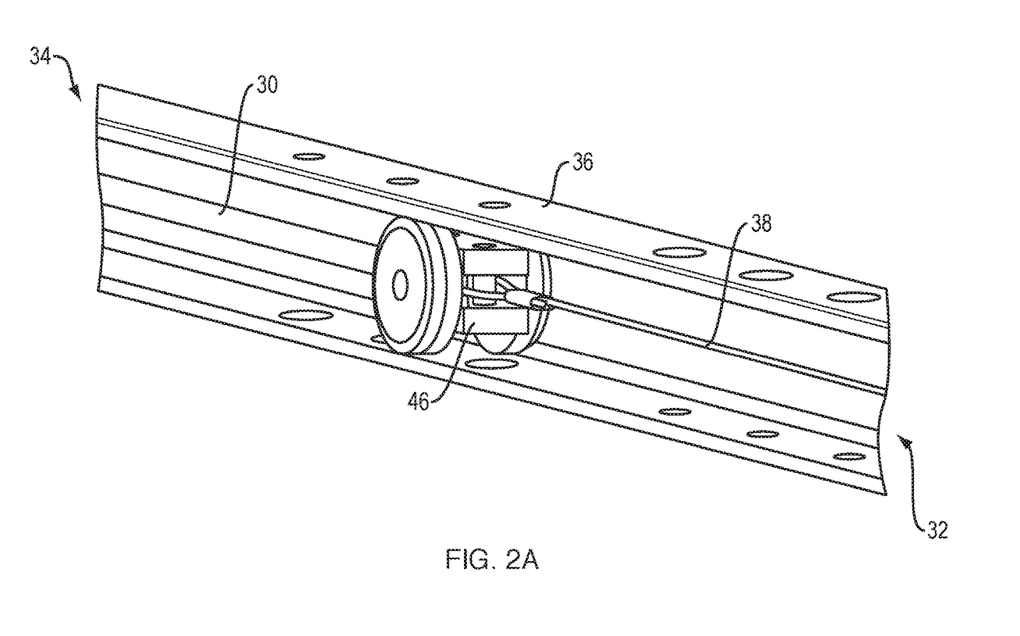
FIGS. 2A-C are detailed views of examples of the boom member of the apparatus of FIG. 1.
Figure 2B:
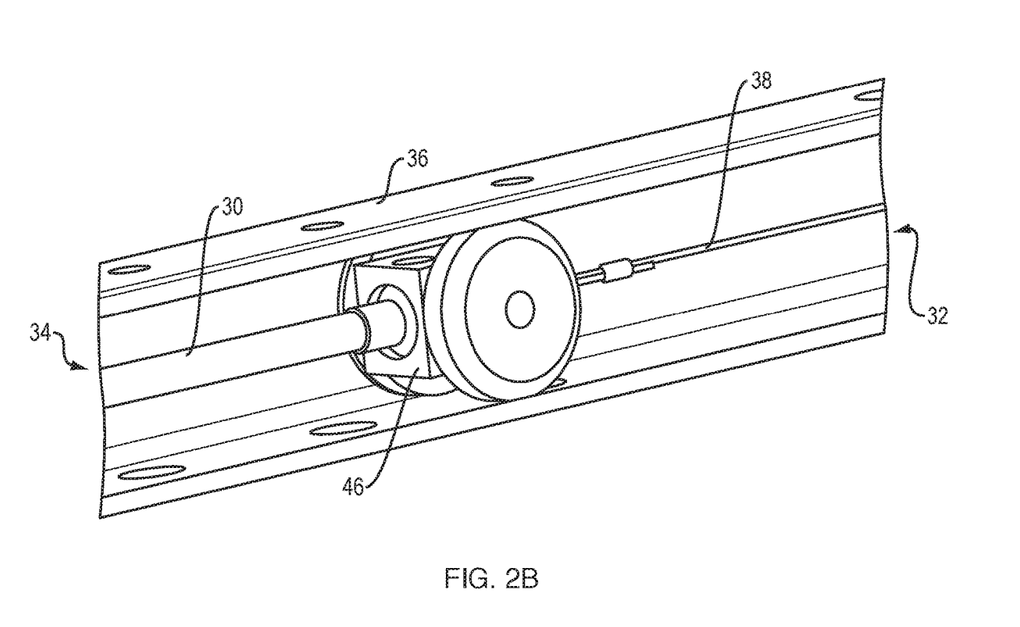
Figure 2C:
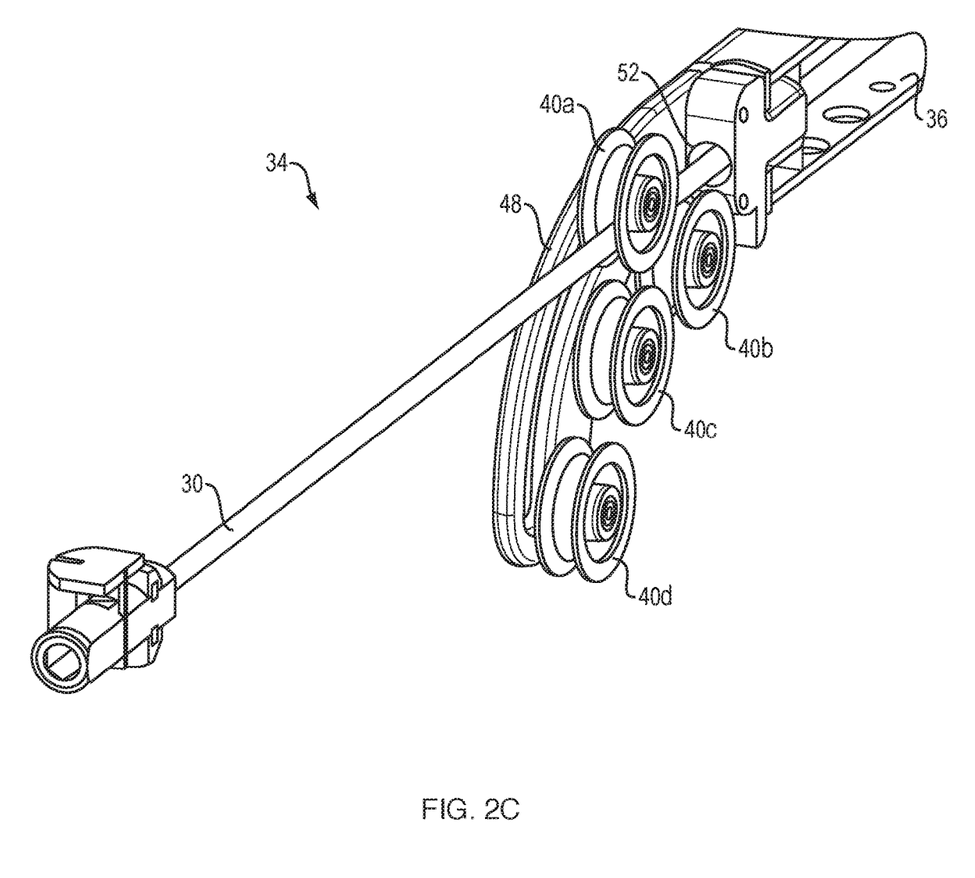

Turning now to FIGS. 2A-C, cut-away, detailed views of the boom member 36 are shown as viewed from the proximal end 32 (FIG. 2A) and the distal end 34 (FIG. 2B-2C). In FIG. 2A, it can be seen that a carriage 46 is disposed within the boom member 36 and configured for axial movement therein. For example, the carriage 46 may be a wheeled carriage. The wire rope 38 is attached a first side of the carriage 46 and extends toward the proximal end 32 of the boom member 36. The drive shaft 30 is attached to the opposite side of the carriage 46 and extends toward the distal end 34 of the boom member 36. Notably, the drive shaft 30 is rigidly mounted to the carriage 46 such that it cannot rotate about its longitudinal axis. Moreover, as shown in FIG. 2C, the drive shaft 30 exits an aperture 52 in the boom member 36 and is routed over a plurality of pulleys 40a, 40b, 40c, 40d housed within an arcuate portion 48 attached to the distal end 34 of the boom member 36. The pulleys 40a, 40b, 40c, 40d provide an additional anti-rotational resistance to the drive shaft 30. While four pulleys are illustrated in FIG. 2C, more or fewer than four pulleys are contemplated by this disclosure.

Figure 3A:
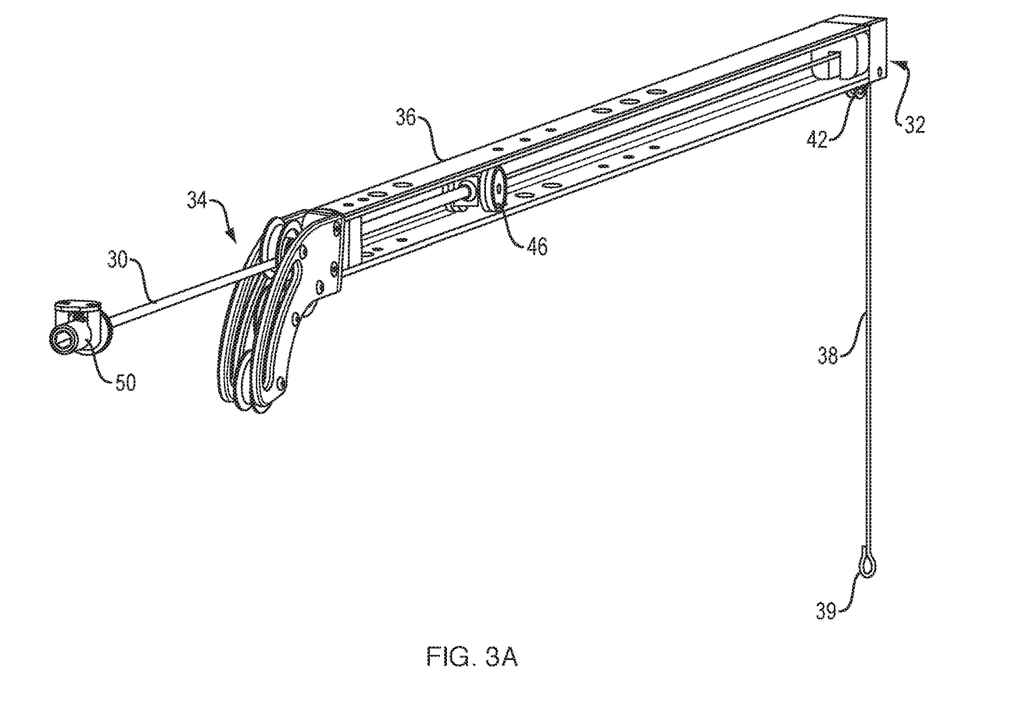
FIGS. 3A-3B are detailed views of the distal end of the boom member of FIGS. 2A-C.

FIG. 3A is a further cut-away, detailed view of the boom member 36 as seen from the distal end 34. At the proximal end 32 of the boom member 36, the wire rope 38 exits through an aperture (not shown) and is routed over a single pulley 42. A hook, thimble or other suitable member 39 is attached to the free end of the wire rope 38 to which counter-weights can be added. At the free end of the drive shaft 30 is a rigidly-mounted receiver 50. In FIG. 3A, the receiver 50 is a hexagonally-shaped female receptor. However, other suitable shapes and configurations of the receiver 50 are contemplated by this disclosure.

Figure 3B:
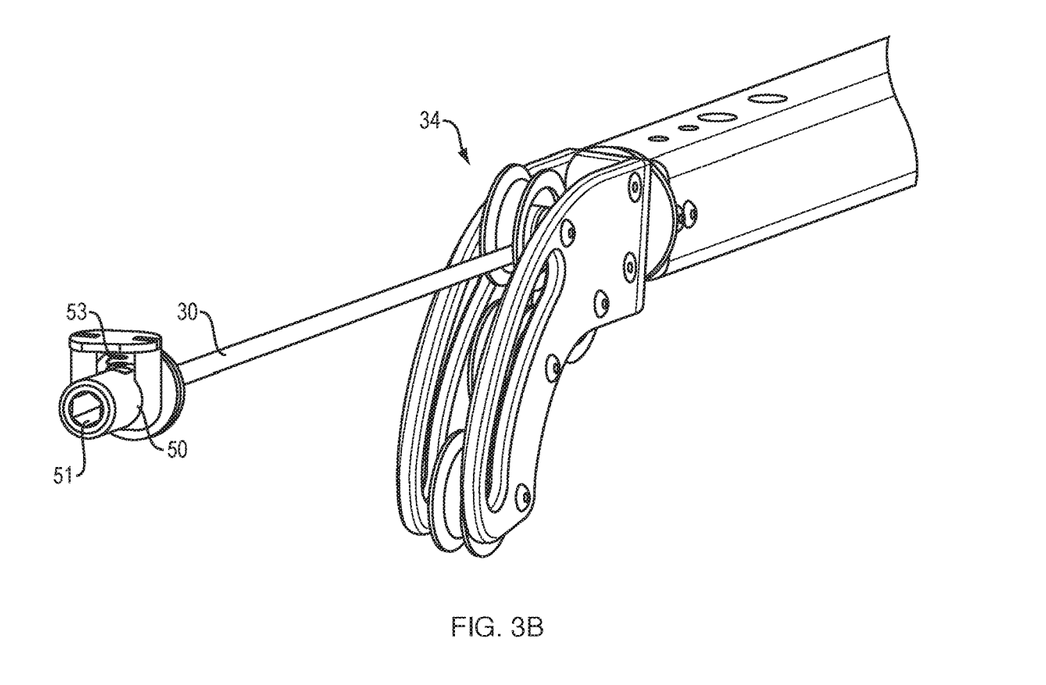

The hexagonal interior surface 51 of the receiver 50 can be seen in more detail in FIG. 3B. As shown in FIG. 3B, the receiver 50 may include a spring 53 or other element for releasable engagement with an insertion member, as further described below. Because the drive shaft 30 cannot rotate about its longitudinal axis, the receiver 50 is advantageously always in the same rotational orientation with respect to the carriage 46. In other examples, not shown, the additional anti-rotation mechanism of the drive shaft 30 could also be built directly into the receiver 50. For example, the resistance to rotation could be achieved by either a custom clutch mechanism or a commercially available clutch mechanism. Thus, drive shaft 30 benefits from freedom in the X, Y and Z directions while still maintaining controlled axial rotation.

Figure 4A:
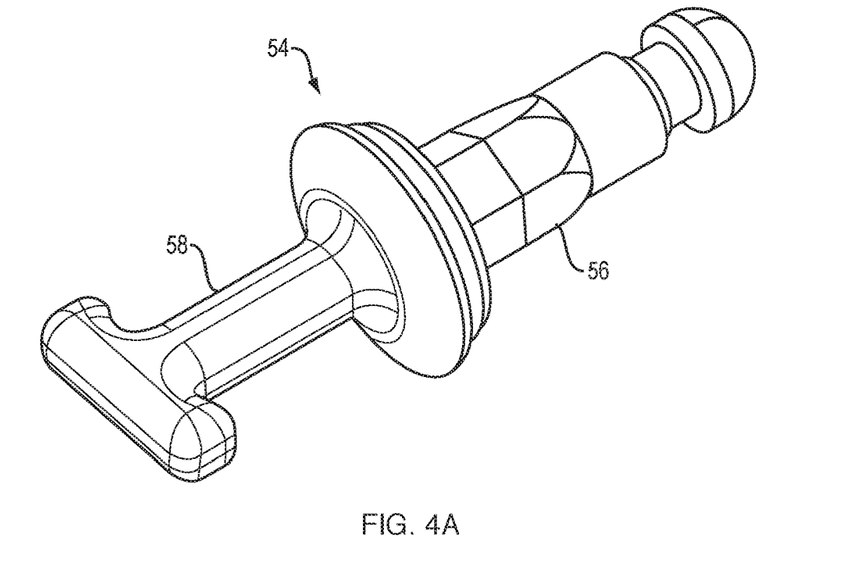
Figure 4B:
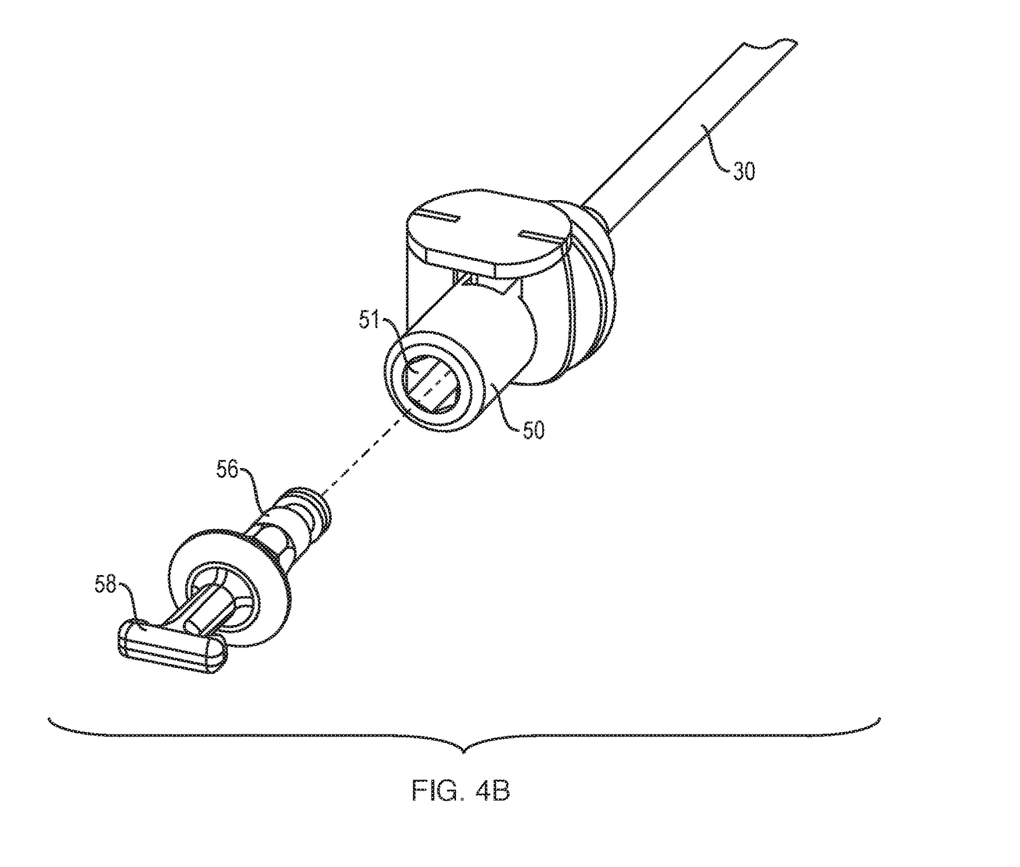

As discussed above, during an operation, a sterile connection is needed to bridge the gap between the non-sterile, durable device and the sterile, patient-contacting drape. As illustrated in FIGS. 4A and 4B, this is accomplished by means of a two-ended sterile connector 54. The sterile connector 54 may be made of polymers, metals or other suitable materials and is intended to be disposed of after use. One end of the sterile connector 54 comprises a pin 56 for insertion into the receiver 50 of the drive shaft 30, as shown in FIG. 4B. For example, the pin 56 may be a hex pin for insertion into the hexagonal interior 51 of the receiver 50. The pin 56 may be releasably secured inside the receiver via the spring 53 (FIG. 3B) or other suitable member. The other end of the sterile connector 54 includes a T-shaped projection 58, the purpose of which will be described in more detail below.

Figure 5A:
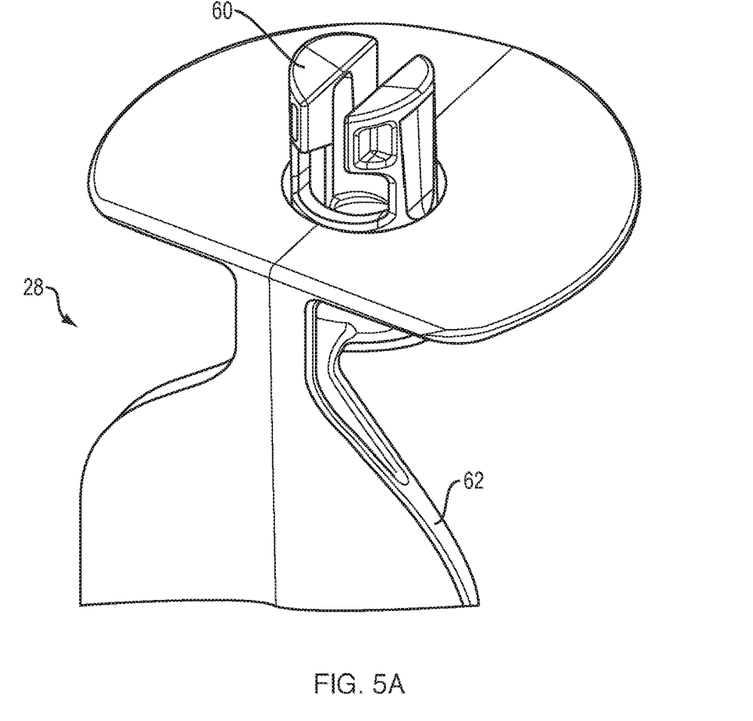
FIGS. 5A-5B illustrate an example of the surgical drape assembly of the apparatus of FIG. 1.
Figure 5B:
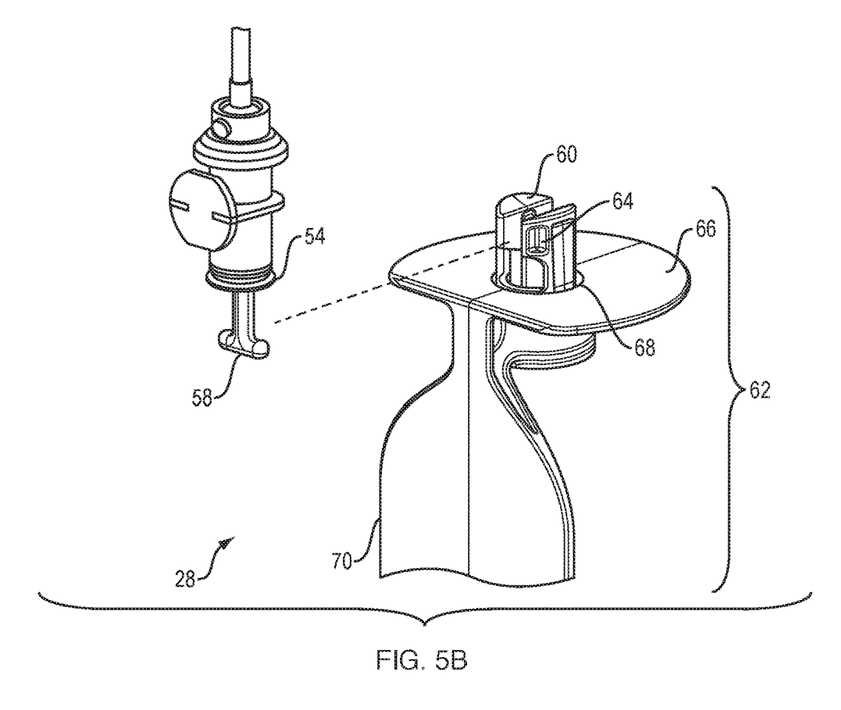

Turning now to FIG. 5A, it can be seen that the disposable drape assembly 28 consists of two parts, a cylindrical portion 60 and a wrap portion 62. Either or both of the cylindrical portion 60 and the wrap portion 62 may be made of polymers, metals, fibers or other suitable materials and are intended to be disposed of after use. As shown in FIG. 5B the cylindrical portion 60 has an aperture 64 at one end configured to accept and align to the T-shaped projection 58, The wrap portion 62 contains a rigid plate 66 with an integrated sling 70, into which the hand of the patient's operative arm is secured. The sling 70 may be made of foam, rubber, fibers or other suitable materials. The rigid plate 66 contains a central aperture 68 for fitting over the cylindrical portion 60. Importantly, the aperture 68 is configured to form an interference fit with the cylindrical portion 60 such that the drape assembly 28 may be rotated against the natural friction between the wrap portion 62 and the cylindrical portion 60. Advantageously, the friction is sufficient to maintain the patient's arm in the new position without requiring that it be manually held in place.

Figure 6:
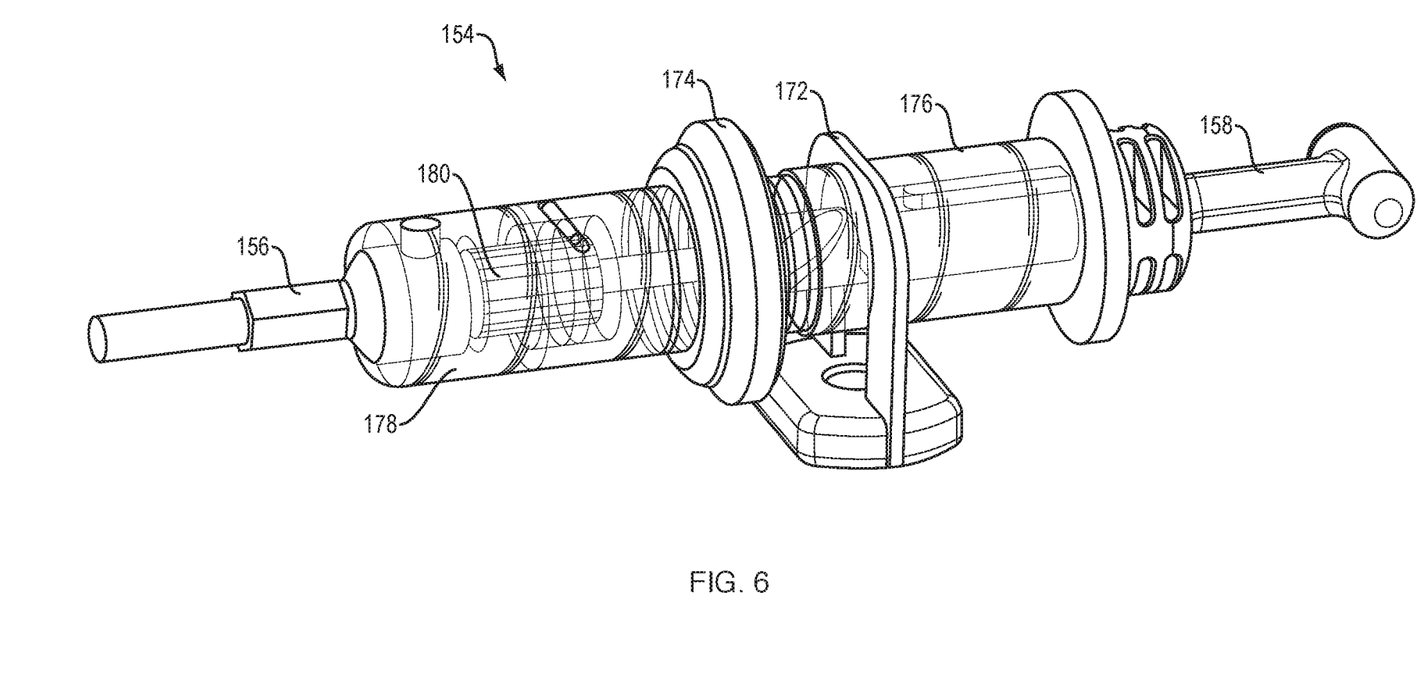
FIG. 6 illustrates an alternative example of the sterile connector of FIGS. 4A-4B.

FIG. 6 illustrates another example of a sterile connector 154 including an alternate anti-rotation mechanism. The sterile connector 154 may form part of the surgical drape assembly (not shown) and may be partially or fully covered by a sleeve (not shown). As seen in FIG. 6, an approximate center of the sterile connector 154 comprises a latch 172 and a latch lock 174. Extending from the latch 172 is a first body portion 176 which is coupled to the T-shaped projection 158. Extending from the latch lock 176 is a second body portion 178 which is coupled to the pin 156. Disposed within the second body portion 178 of the sterile connector 154 is a torque insert 180. The torque insert 180 is may be a commercially-available torque insert, such as a TI-300 Series Torque Insert manufactured by REELL Precision Manufacturing, Inc., St. Paul, Minn., incorporated herein by reference. The torque insert 180 is connected to the pin 156 on one end and the T-shaped projection 158 on the other end. The torque insert 180 is non-sterile and is intended to be reusable. In this example, the anti-rotation mechanism of the disposable drape assembly 28, as discussed above with regard to FIG. 5B, is thus directly incorporated as part of the sterile connector 154. Advantageously, this configuration reduces variability in the torque value due to component variations and environmental conditions (e.g., wet or dry) and also reduces costs of manufacturing. Additionally, it allows the entire surgical drape assembly to be disposable.

Figure 7:
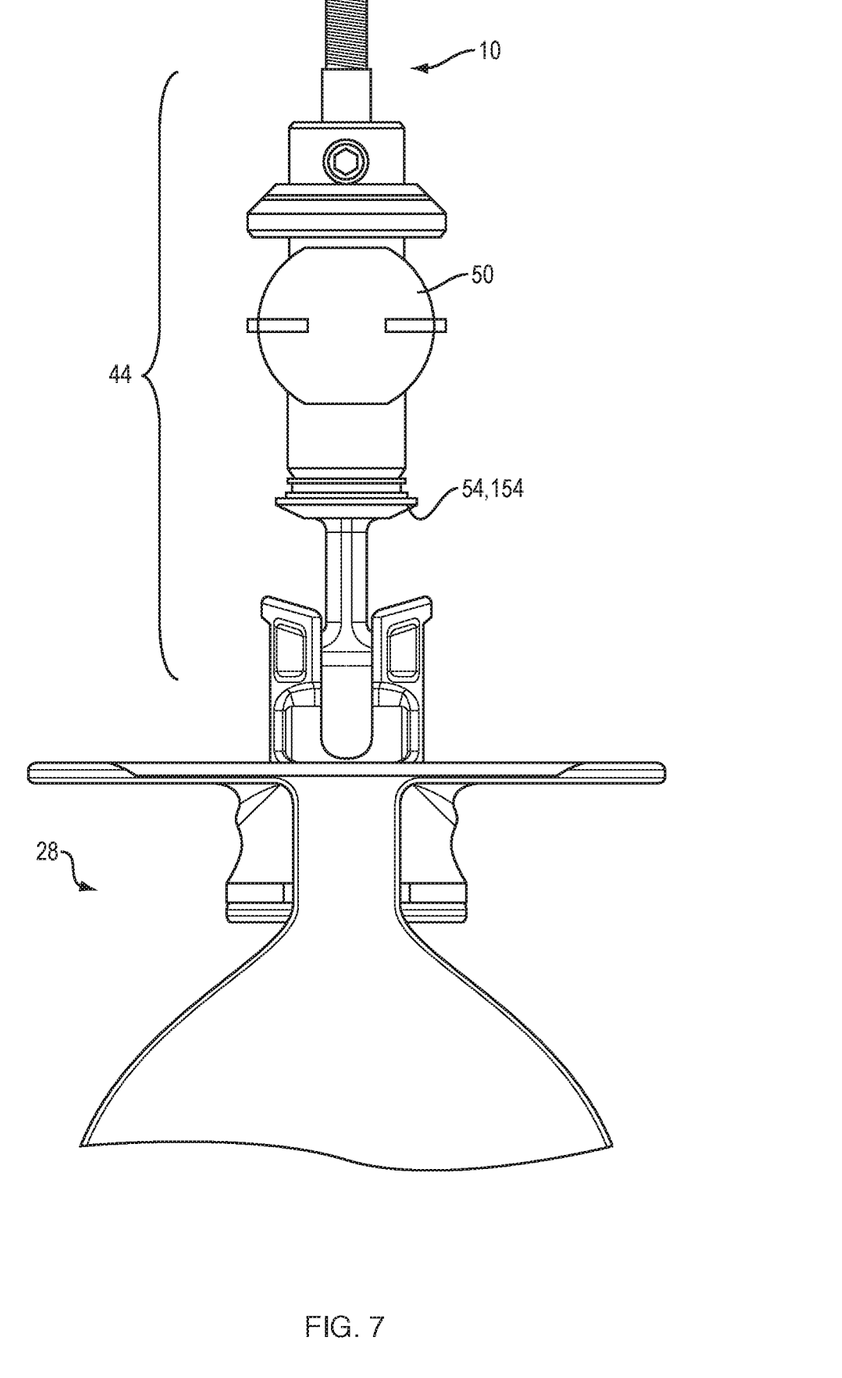
FIG. 7 illustrates the connector assembly attached to the surgical drape assembly and the limb positioning apparatus of FIG. 1.

FIG. 7 illustrates the complete connector assembly 44 (i.e., the receiver 50 and the connector 54, 154) attached to both the limb positioning apparatus 10 and the surgical drape assembly 28 as depicted in FIG. 1. The connector assembly 44 advantageously allows the surgeon to operate the limb positioning apparatus 10 during surgery without compromising the sterile field. Additionally, the operative arm of the patient can be attached to and detached from the limb positioning apparatus 10 without compromising the sterile field.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical limb positioning apparatus comprising:
   an elongated, hollow boom member having a proximal end, a distal end and a longitudinal axis extending therebetween;
   a carriage disposed within the boom member and moveable along the longitudinal axis;
   a first flexible member attached to a first side of the carriage and exiting the boom member at a first aperture located at the proximal end of the boom member, a free end of the first flexible member configured for attachment to a weight;
   a second flexible member attached to a second side of the carriage such that the flexible member cannot rotate relative to the longitudinal axis of the boom member, the second flexible member exiting the boom member at a second aperture located at the distal end of the boom member; and
   a connector assembly attached to a free end of the second flexible member for forming a sterile connection to a drape assembly;
   wherein one of the connector assembly and the drape assembly comprises an anti-rotation mechanism configured to maintain an operative limb of a patient in a pre-selected position.

2. The apparatus of claim 1, wherein the connector assembly comprises a receiver attached to the free end of the second flexible member and a connector for releasably coupling to the receiver.

3. The apparatus of claim 2, wherein a first end of the connector comprises a pin, and the receiver comprises an opening for receiving the pin.

4. The apparatus of claim 2, wherein a second end of the connector comprises a projection, and the drape assembly comprises an aperture for releasably coupling to the projection.

5. The apparatus of claim 2, wherein at least a portion of the connector is sterile.

6. The apparatus of claim 2, wherein the anti-rotation mechanism is a torque insert disposed within the connector.

7. The apparatus of claim 1, wherein the boom member is a generally square tube.

8. The apparatus of claim 1, wherein the carriage is a wheeled carriage.

9. The apparatus of claim 1, wherein the first flexible member is a wire rope.

10. The apparatus of claim 1, wherein the second flexible member is a metal cord.

11. The apparatus of claim 1, further comprising an arcuate portion attached to the distal end of the boom member, the second flexible member being routed through a plurality of pulleys housed within the arcuate portion, the pulleys providing an additional anti-rotational resistance to the second flexible member.

12. A method of positioning a limb during surgery, comprising:
   disposing an operative limb of a patient within a drape assembly of a limb positioning apparatus, the limb positioning apparatus comprising:
      an elongated, hollow boom member having a proximal end, a distal end and a longitudinal axis extending therebetween;
      a carriage disposed within the boom member and moveable along the longitudinal axis;
      a first flexible member attached to a first side of the carriage, the first flexible member exiting the boom member at a first aperture located at the proximal end of the boom member, a free end of the first flexible member configured for attachment to a weight;
      a second flexible member attached to a second side of the carriage such that the flexible member cannot rotate relative to the longitudinal axis of the boom member, the second flexible member exiting the boom member at a second aperture located at the distal end of the boom member; and
      a connector assembly attached to a free end of the second flexible member, the connector assembly for forming a sterile connection to the drape assembly, one of the connector assembly and the drape assembly comprising an anti-rotation mechanism; and
   rotating the operative limb of the patient to a pre-selected position;
   wherein the anti-rotation mechanism is configured to maintain the operative limb of the patient in the pre-selected position.

13. The method of claim 12, wherein the connector assembly comprises a receiver attached to the free end of the second flexible member and a connector for releasably coupling to the receiver.

14. The method of claim 13, wherein a first end of the connector comprises a pin, and the receiver comprises an opening for receiving the pin.

15. The method of claim 13, wherein a second end of the connector comprises a projection, and the drape assembly comprises an aperture for releasably coupling to the projection.

16. The method of claim 13, wherein at least a portion of the connector is sterile.

17. The method of claim 13, wherein the anti-rotation mechanism is a torque insert disposed within the connector.

* * * * *